United States Patent
Dalal

(10) Patent No.: US 11,495,356 B2
(45) Date of Patent: Nov. 8, 2022

(54) PROGRAMMED COMPUTER WITH ANTI-DEPRESSION TOOLS

(71) Applicant: Aashna Dalal, Porter Ranch, CA (US)

(72) Inventor: Aashna Dalal, Porter Ranch, CA (US)

(*) Notice: Subject to any disclaimer, the term of this patent is extended or adjusted under 35 U.S.C. 154(b) by 113 days.

(21) Appl. No.: 16/554,907

(22) Filed: Aug. 29, 2019

(65) Prior Publication Data

US 2021/0065910 A1  Mar. 4, 2021

(51) Int. Cl.
| | | |
|---|---|---|
| *G16H 20/70* | (2018.01) | |
| *G16H 50/50* | (2018.01) | |
| *G16H 10/20* | (2018.01) | |
| *G16H 50/30* | (2018.01) | |
| *G06V 40/10* | (2022.01) | |
| *G06V 40/20* | (2022.01) | |

(52) U.S. Cl.
CPC ............ *G16H 50/50* (2018.01); *G06V 40/10* (2022.01); *G06V 40/20* (2022.01); *G16H 10/20* (2018.01); *G16H 20/70* (2018.01); *G16H 50/30* (2018.01)

(58) Field of Classification Search
CPC ......... G16H 10/60; G16H 40/20; G06Q 10/10
See application file for complete search history.

(56) References Cited

U.S. PATENT DOCUMENTS

| | | | | |
|---|---|---|---|---|
| 6,132,724 A | * | 10/2000 | Blum | A61K 33/24 424/725 |
| 2004/0210159 A1 | * | 10/2004 | Kibar | A61B 5/165 128/898 |
| 2016/0027278 A1 | * | 1/2016 | McIntosh | G08B 21/0423 715/741 |
| 2017/0017759 A1 | * | 1/2017 | MacNeice | G16H 70/20 |
| 2018/0350455 A1 | * | 12/2018 | Rosen | G16H 10/60 |

* cited by examiner

*Primary Examiner* — Reginald R Reyes
(74) *Attorney, Agent, or Firm* — Law Office of Scott C Harris, Inc

(57) ABSTRACT

A system of monitoring depression in a user, uses a computer system. The system initially calibrates, to determine baseline information about the user for each of a plurality of different categories of action of the user and continues learning about the user to make minor adjustments to prescribed behaviors and therapies. The categories can include sleep, diet, screen time, exercise, social interaction, medication compliance, and academic performance. The computer system uses the baseline information to determine user behavior, for each of the different categories that is correlated with likely behavior associated with depression. After initially calibrating, the computer system operates to monitor each of said different categories of action of the user and compares the monitored categories with the baseline information to determine whether the user is complying by acting within specified parameters within each category. The system can provide positive reinforcement and alerts.

14 Claims, 5 Drawing Sheets

PROGRAMMED COMPUTER WITH ANTI-DEPRESSION TOOLS

BACKGROUND

Depression is a common mental disorder, especially among younger people. According to the Center for Disease Control and Prevention (CDC), as of 2016, suicide was the second leading cause of death for adolescents, ages 10-24. According to the US Department of Health and Human Services, about 60 percent of people who commit suicide have had a mood disorder such as depression. This makes depression, and the treatment of depression, a national emergency.

Depression can also be associated with symptoms that can include feelings of hopelessness, loss of interest, fatigue, restlessness, shifts in appetite and weight, problems sleeping, and others.

Antidepressants can be used to attempt to combat both depression and its symptoms. However, many of the antidepressant drugs have their own host of side effects, and many people will simply refuse to take the antidepressants.

It has been postulated that adolescents who spend time on screen activities are more likely to have depression and its symptoms. Consequently, depression is becoming an even more common affliction among younger people. The reliance on screen-based devices such as phones and tablets, and more specifically, the reliance on social media as an escape from real life, may also be factors.

SUMMARY

Based on the inventor's recognition that reliance on computers is actually worsening the depression crisis, the inventor has created an application, which can provide a personalized routine and treatment/management plan for individual users. Users who rely on computers can easily use this computer-based system. The programmed machine, in certain embodiments, may carry out monitoring/compliance, positive reinforcement, and alerting different people, depending on the severity of deviation from the treatment plan.

An object of the embodiments is to address depression, especially in teens and young adults, ages 12 to 24. The embodiments describe a smart system using artificial intelligence and machine learning to address depression in new ways that current versions of therapy and medication are unable to do.

In an embodiment, there are 4 main aspects of the programmed computer, including calibration, monitoring/compliance, positive reinforcement, and an alert/notification system. Calibration is collecting baseline data to personalize the user's treatment plan and improve accuracy. Calibration is part of the monitoring/compliance aspect since it uses sensor data. Monitoring/compliance is ensuring that the user is following the prescribed treatment plan. Positive reinforcement is a tool to motivate users and improve adherence to prescribed therapy. The alert/notification system notifies another party e.g. a family member or a professional of the user's progress as explained herein.

BRIEF DESCRIPTION OF THE DRAWINGS

The different figures show different embodiments in which.

DETAILED DESCRIPTION

An embodiment provides a personalized routine and treatment/management plan for individual users. In an embodiment, the computer initially calibrates based on the measured level of depression to determine baseline parameters for monitoring/compliance. After initial calibration, the system will continue to calibrate and make minor adjustments to the user's prescribed treatment plan. The overall calibration procedures are described later for individual categories of the monitoring/compliance aspect.

An embodiment also includes a notification system ensuring that the user's progress is continually tracked and ensuring that an appropriate person will receive alerts if the user's condition is worsened or in a state where it is believed likely to worsen in the future.

Figure 1:
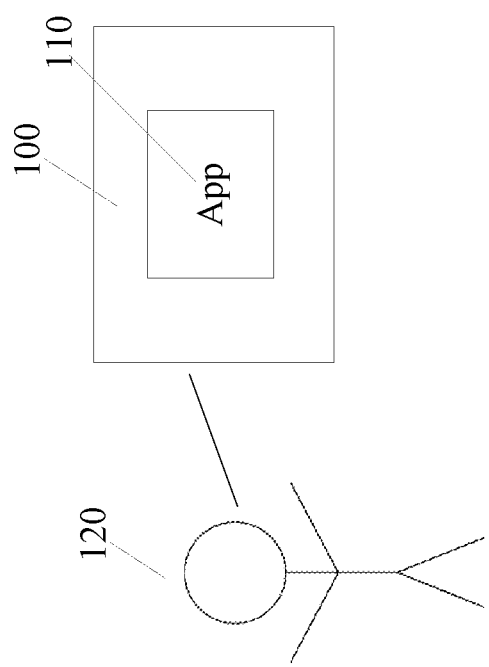
FIG. 1 shows the app running on a computer being used by a user.

An embodiment is explained with relative reference to the figures. In FIG. 1, a computer system 100, which is a local client, is shown running the application 110 under control of the user 120. The client 100 can be any kind of computer including a desktop computer, phone, tablet, or any other computer. The computer also communicates as explained herein over a wired or wireless Internet connection. All data is stored on a secure cloud for backup, restoration, population analytics, and to allow the user to access the app on multiple platforms.

Figure 2:
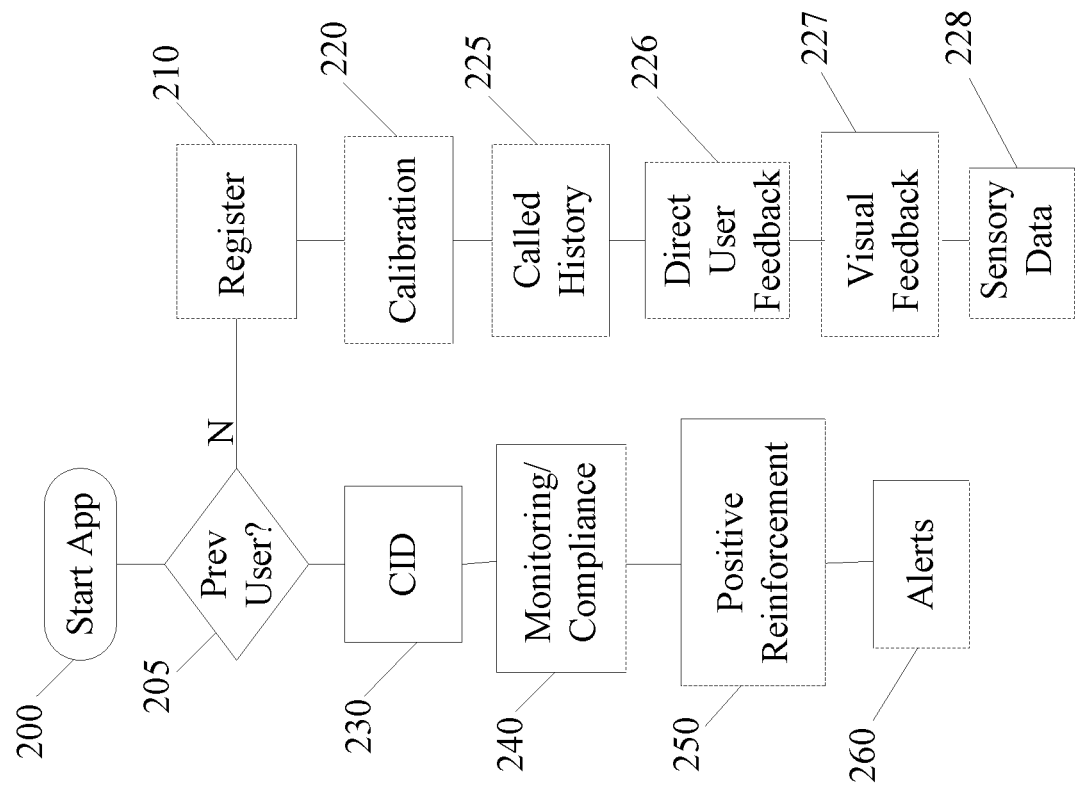
FIG. 2 shows an overall flowchart of the operation of the app

The operation starts at 200 in FIG. 2 where the app is started on the computer. At 205, the computer determines if this is a previous user. If not, the user is prompted to register at 210, including the user's name, phone number, age, gender, and identifying information such as a password. The system can also use the biometric identification module on the computer platform, such as Apple face ID, fingerprint, or some other platform specific engine, to identify the user. This complies with HIPAA requirements, by ensuring that no information from the app is given to anyone but the authorized users.

After registration at 210, the system goes to calibration at 220.

Prior to being able to personalize the features of the product for a specific individual, there is an initial calibration period at 220 during which the app gathers baseline data regarding the user's specific routines and behaviors. The calibration is used to determine whether the user is in compliance with various categories, as explained herein.

First, at 225 the system collects the medical history of the user. The medical history may include a user questionnaire to notify the system of any comorbidities, previous hospitalizations, medications, family medical history, etc.

As an alternative to doing this during calibration, this can be done during registration at 210. The length of the initial calibration period will vary depending on the category and the user. If the user exhibits fairly consistent behaviors over time, the initial calibration period may be shorter. However, if the user has an irregular routine with significant changes in behavior, the initial calibration period may be longer as it will take more time to gather sufficient data on the user. For example, the category of sleep may require the system to collect data over an initial period of time, e.g., 2 weeks, to gauge the user's current sleeping patterns, sleep requirements, and gauge how the user's behaviors and routine are correlated with sleeping patterns.

An example of another category is academic performance. Under this category, the system will ask for the user's grades from previous years and use them as a benchmark to monitor trends in future grades and academic performance.

In general, calibration uses three main ways of gathering data. Direct user feedback at 226 relies on user reported outcomes and data collected from user questionnaires. For example, the questionnaires may include questions about the user's emotions, sleeping patterns, and other habits.

Data can also be gathered by visual feedback at 227, which is carried out by reading the user's emotions and moods based on changes in the user's physical appearance. This can be done for example using a camera, facial recognition techniques, and machine learning which can allow the system to measure the severity of changes in the user's behavior. For example, if the visual feedback consistently captures the user with baggy eyes and dark lines, it can conclude that something is wrong with the sleeping habits that needs to change.

Visual feedback may also be able to detect weight loss or gain, concluding that the user's dietary habits need to be adjusted. It may also detect discoloration in the user's face due to possible stress. The system may also be able to mark when the user may have been crying, possibly conveying that the user is struggling with social issues. Another example is that visual feedback could notice when the user's eyes are dilated, conveying excitement, or if the user's pupils are contracted, possibly conveying anger. Overall, visual feedback can detect constant changes in the user's mood and emotions based on their facial expressions.

Sensory data is also collected at 228, using existing smart devices and applications which may be on the computer 100 or on other platforms. Examples of a smart device are a smart phone, a smart bed, a smart scale, a fitness tracker, or a smart watch. A smart phone allows the system to aggregate and process data from various sensors. A smart bed can measure quality and length of sleep. A smart scale can track changes in a user's weight, BMI, and biometric measurements such as body fat percentage and water percentage. A fitness tracker can measure activity and heart rate. In addition to these two, a smart watch can also measure arrhythmia burden. Calibration at 220 is used to learn the user's sensitivities and specificities so that the system can create a personalized solution for the user. In addition, the system can use this information to determine how closely the user needs to be monitored. One way to do this is by asking the user to provide a depression score based on a standard depression test such as the PHQ-9 to analyze the severity of their depression when registering for the app. The PHQ-9 is a quick depression assessment that the user can take prior to registering for the app. The PHQ-9 test labels users under five categories of depression severity: minimal or none, mild, moderate, moderately severe, or severe. Based on the category that the user falls into, the system will determine how closely the user needs to be monitored. Additionally, the PHQ-9 score can be used to create goals for the user, which is described herein.

After the user has been registered at 205, the system checks the identity of the user at 230, to determine that the correct user is actually using the app, and to maintain HIPAA compliance. After passing the check ID step, flow passes to the monitoring and compliance at 240.

An embodiment describes monitoring seven central categories, related to actions of the user, biological functions of the user, and activities being done by the user:

sleep (actions)
diet (actions)
screen time (activities)
exercise (activities)
social interaction (activities)
medication compliance (actions)
academic performance (activities)

Prior to monitoring and determining compliance with each of these categories, the system needs to find baseline information about the category in order to determine whether the user is outside of that baseline. In an embodiment, for each of these categories, the system first calibrates at 220, to determine that baseline information. In an embodiment, the calibration uses direct user feedback, visual feedback, and sensory data to determine the user's current routine and behaviors.

In an embodiment, the calibration may be repeated during normal operation, to fine tune the baseline, and also to adjust for changes in the baseline.

Then, the system determines what is optimal for the user based on their initial status including their depression score and overall behaviors. Using machine learning, the system will determine the ideal sleep schedule for a user by learning about the user's internal body clock. Everyone has an internal circadian biological clock that causes them to feel more tired and more awake at different times of the day. Some may feel sleepiest during the time intervals of 5-7 AM and 2-5 PM while others may feel most tired during the time intervals of 3-5 AM and 1-3 PM. These timings are different for each individual. This internal body clock can be determined by tracking when the user sleeps and wakes up on a regular basis without an alarm or any other electronic gadgets. It can also monitor if the user takes naps regularly. After collecting this data, the system will recommend a schedule that corresponds to the user's internal circadian biological clock to ensure that their sleep schedule is more natural rather than forced. Exceptions for this would be if the user is clearly sleeping too much or too little due to other symptoms of depression. The system also determines how to enforce it as part of the monitoring/compliance aspect to improve adherence to the user's prescribed therapy.

The system sets goals for each category and measures the user's compliance and performance. For example, using the user's self-reported PHQ-9 score, the system sets a target score for the user to reach over a certain period of time. The PHQ-9 uses a scale of 0-27 with 27 being the most severe case of depression. For example, if a user's initial score is 16, the user would fall under the category of moderately severe depression. As a result, the system might set a target score of 13 to improve the user's status from moderately severe to moderate depression.

Figure 3:
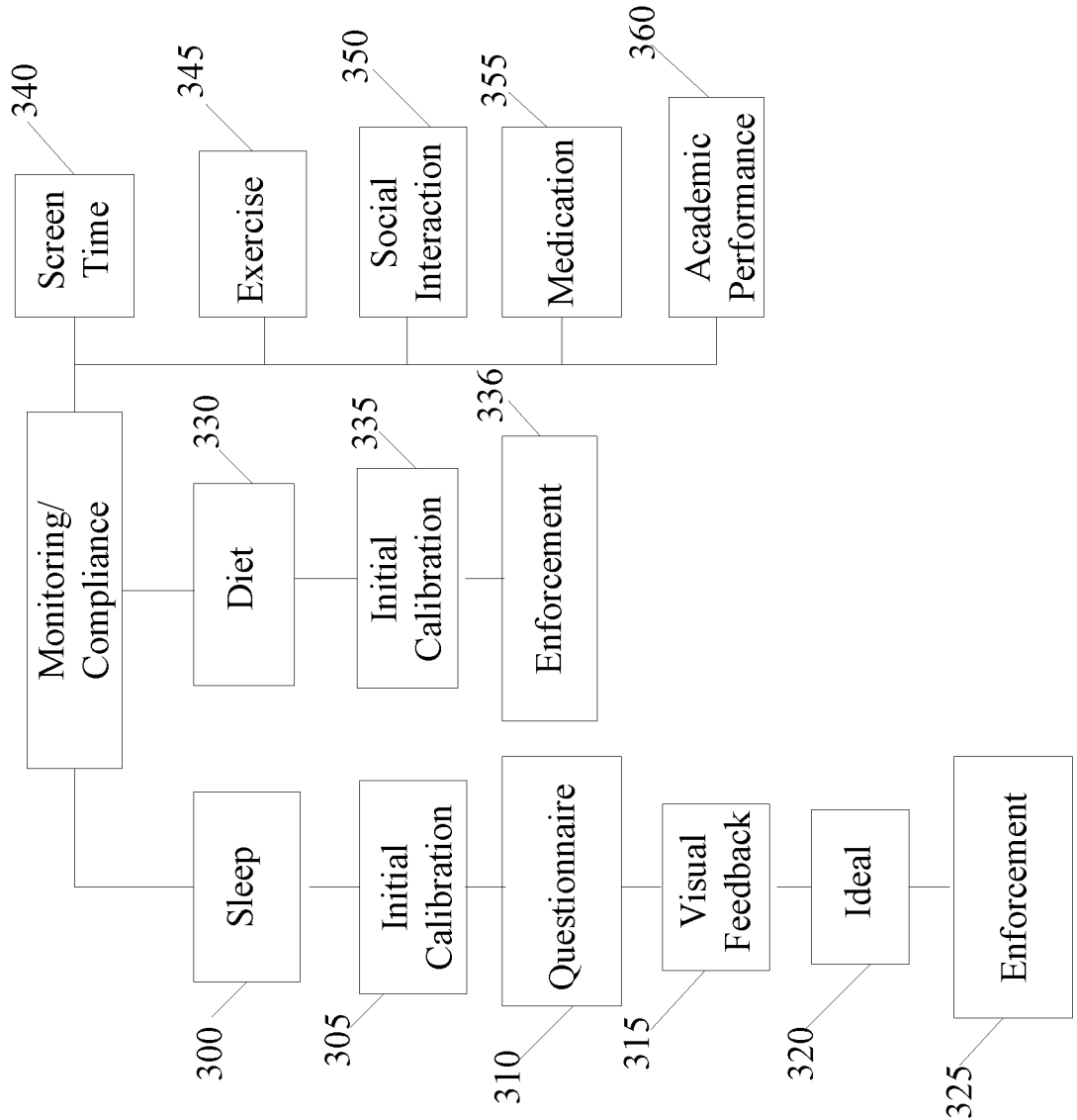
FIG. 3 shows a flowchart in further detail of the monitoring and compliance.

FIG. 3 illustrates the data collection and enforcement features of each of the seven categories, which is carried out after the calibration. FIG. 3 illustrates the basic monitoring and compliance steps carried out according to the machine according to an embodiment.

The first category at 300 is the category of sleep. The system first carries out initial calibration at 305, which looks at the user's current sleep schedule. This looks for, in an embodiment:

The Number of Hours That the User Sleeps
The user's sleep timing (by tracking wake-up and sleeping time), and The User's Quality of Sleep The current number of sleep hours and sleep timing, can be tracked using metadata from applications and sensors on a smartphone or a smart bed. In addition, this can be obtained via manual requests, such as from a user questionnaire regarding how much sleep they get in relation to how they feel on a daily basis. This data will be correlated to the metadata to determine the user's quality of sleep so the system can develop the ideal routine for the user. Metadata can include data collected from a smart bed including movement, the number of times the user woke up, the number of times the user got up to use the restroom, or the number of times the user woke up to glance at their phone. This data is matched with the user's answers on the questionnaire to eliminate discrepancies and receive the most accurate representation of the user's quality of sleep. After processing this data and keeping track of days during which the user is in a good mood or exhibiting positive behaviors, the system creates an ideal sleep schedule for the user.

In addition, this correlates to the data collected by the visual component of the system at 315. In one embodiment, the system tracks the user's facial expressions on a daily basis to determine when the user looks dispirited or tired versus more awake and alert. For example, the system can use a software such as facial recognition software on smartphones to assess and interpret changes in the user's facial expressions and to characterize those facial expressions as happy and contented expressions, in one embodiment. In another embodiment, the system compares current facial expressions to previous expressions, and uses knowledge of those previous times to determine how the user feels currently. For example, when it has been correctly diagnosed that the user is feeling good (not depressed) then facial expressions associated with this good time can be added to a database of not depressed facial expressions. Conversely, previous diagnoses of depression can make facial expressions of depressed times. In one embodiment, this can use the face recognition API that is already present in the phone, such as Apple's face recognition API. After collecting this data, the system determines the ideal sleep schedule for the user at 320.

Enforcement follows at 325, in which the system controls smart home features such as lighting, a smart alarm, and music to enforce the sleep schedule. The lights are controlled to run on a smart timer that turns on and off according to the user's recommended sleeping and waking up times. There is an automatic alarm set for every morning with uplifting music to wake the user up and start the day on a positive note. The system also sets to play more soothing/calming music at night to help the user sleep at the right time.

In a similar way, the system recommends and monitors diet at 330.

In learning about the user's current eating habits at 335, the embodiment looks for three main things: the user's weight, the user's food intake (type of food, amount of food, etc.), and the times at which the user eats. To collect this data, the system uses direct user feedback through questionnaires as well as metadata from other applications on a smartphone to accurately capture the user's current diet. The system also uses data from a smart scale to monitor any changes in the user's weight. Using this information, the system creates a balanced diet that is appropriate for the user and will recommend food type, amount, and timings. The system prescribes a balanced diet based on the amount of protein, carbs, fruits, vegetables, and other food groups that are necessary for each user. For example, according to the dietary guidelines for Americans, teenage girls should consume about 2.5 cups of vegetables, 1.5 cups of fruits, 6 ounces of grains, 3 cups of dairy, and 5 ounces of protein foods daily (U.S. Department of Health and Human Services and U.S. Department of Agriculture). Secondly, based on the user's weight/BMI, the system sets a calorie count for the user and adjusts the user's number of servings accordingly. The system also sets times for the user to eat at to ensure that the user does not skip meals or binge eat. The smart alarm system also notifies the user when it is time to eat as its enforcement technique at 336.

Screen time is monitored at 340. In learning about the user's current screen usage, the embodiment monitors and tracks the number of hours of screen usage, the time of day, and social media usage. To collect this data, the system uses metadata from the user's smartphone. Using this data, the system determines the amount of screen time that is appropriate for the user and operates to block applications on the phone or other electronic devices once this limit has been reached. Essentially, the system will attempt to reduce the quantity of screen time, while improving the quality of usage. The system will improve quality of screen time by differentiating between productive and unproductive activity that requires screen usage. For example, it will restrict excessive usage of multiplayer games; however, it will allow multiuser collaboration tools with minimal restriction. The system will reduce quantity of screen usage by creating goals for the user to accomplish gradually. For example, if a user's average screen time per day is four hours, the system can start by blocking their phone after three hours of usage. In general, the system can try to reduce screen time by no more than 25% a week, for example. Additionally, the system will block any electronic devices during the user's allotted sleep time by keeping note of the user's recommended sleeping time and wake-up time.

Exercise is monitored at 345. In learning about the user's current habits, an embodiment monitors and tracks the amount of physical activity that the user engages in and how often. To collect this data, the system uses metadata from the user's smartphone as well as a fitness tracker or a smartwatch, along with a user questionnaire. As described above, a smartwatch and fitness tracker provide data such as heartrate, physical activity, and arrhythmia burden. Using this data, the system creates an exercise routine for the user to ensure that the user engages in sufficient physical activity. These goals are adjusted in the right direction in small steps based on the user's needs and health status. For example, if the user is initially not physically active at all, they will be encouraged to start by exercising once to twice a week for small periods of time. Eventually, the goals will strive to achieve published medical guidelines for recommended physical activity. The smart alarm/reminder system reminds the user of when they need to exercise. The user will also be kept motivated through the system's positive reinforcement features described herein.

The system monitors social interaction at 350. In order to learn about the user's social engagements, the system primarily uses direct user feedback through the form of questionnaires. The system tracks how the user feels on days which they have more social interaction. The system can also use a friends in proximity feature on a smart phone which monitors locations of friends of the user in order to automatically track the user's social interactions. The system will then track the user's visual feedback (e.g. is the user smiling?) and overall mood on days that the user is socially engaged to determine the impact of social interaction on the user's wellbeing. The initial calibration period uses visual feedback features, a friends in proximity app, and user questionnaires to determine appropriate modes of social interaction for the user. For example, the system may suggest activities such as local community service projects, team sports, or other interest-based activities to motivate the user to increase their social involvement. The user will be further motivated to complete social interaction goals through positive reinforcement features.

Medication compliance is monitored at 355. This is based on the user's input on the initial medical history questionnaire. The system will determine what medication the user has been prescribed and when they are supposed to take it. Electronic prescriptions can also be used for capturing the necessary information. With the information on the prescriptions, the system will input the times at which the user needs to take his/her medicine into an inbuilt calendar program. The system's smart alarm/reminder system then enforces that the user stays on schedule and takes their medicine at the appropriate times using the data in the calendar. With smart bottle usage, the system can also measure compliance by tracking the amount of medicine that remains in the bottle periodically. Smart pill bottles track when a user takes their medication by noting when the pill bottle is opened or closed, and uses wireless communication to transmit data to a connected device. Using this information, the smart reminder system can then notify the user when they need to refill their medication to ensure that the user never misses a day due to the unavailability of medications.

Academic performance is monitored at 360. The system initially asks the user for their transcript from previous years to get an idea of the user's capability and current academic standing. For this category, the system continues to track and monitor the user's grades and academic performance and looks out for any major and unexpected changes. If this occurs, the alert/notification system will take action accordingly. The positive reinforcement features also encourage the user to maintain their grades.

Figure 4:
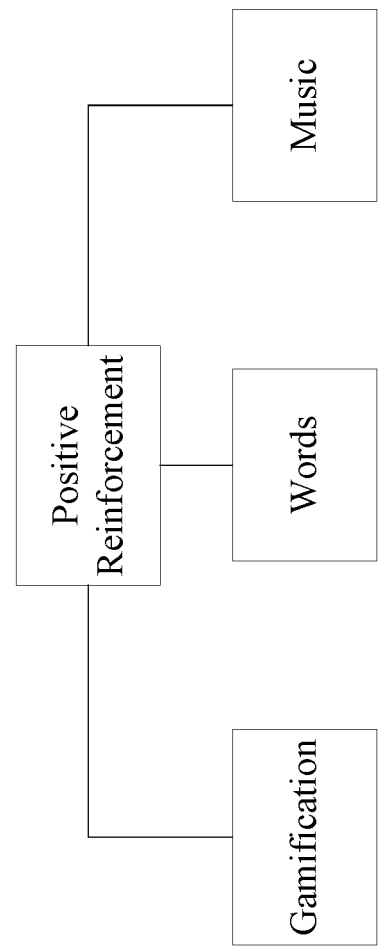
FIG. 4 shows a top level flowchart of the positive reinforcement.

One important feature of the system is the positive reinforcement techniques at 250, as shown in more detail in FIG. 4. Positive reinforcement and in different embodiments can include gamification, positive feedback using encouraging words, and uplifting music. In one embodiment, this product is largely targeted towards teens and young adults, prioritizing gamification as a positive reinforcement tool. Gamification is meant to increase user engagement, motivate the user to stay on track, and encourage overall compliance to the user's prescribed routine. It uses game design elements such as a point system and badges and awards to motivate the user to accomplish their compliance goals. Users will also be able to make in-app purchases with their earned points to gain a sense of accomplishment. Additionally, the present invention serves as a friendly companion to the user and can lift the user's spirits whenever they are feeling down with the use of optimistic and uplifting quotes/ statements.

Embodiments also use artificial intelligence to converse with the user if the user ever needs someone to talk to. For example, the system can use artificial intelligence bots such as Alexa or Ski to carry out conversations with the user. The use of these bots may allow human-like conversation, including regular conversation for positive feedback. They will also summon immediate help in times of major crises such as suicidal thoughts. Music is another part of the positive reinforcement technique. The system will have several inbuilt playlists and meditations to choose from to calm the user or elevate their mood.

Figure 5:
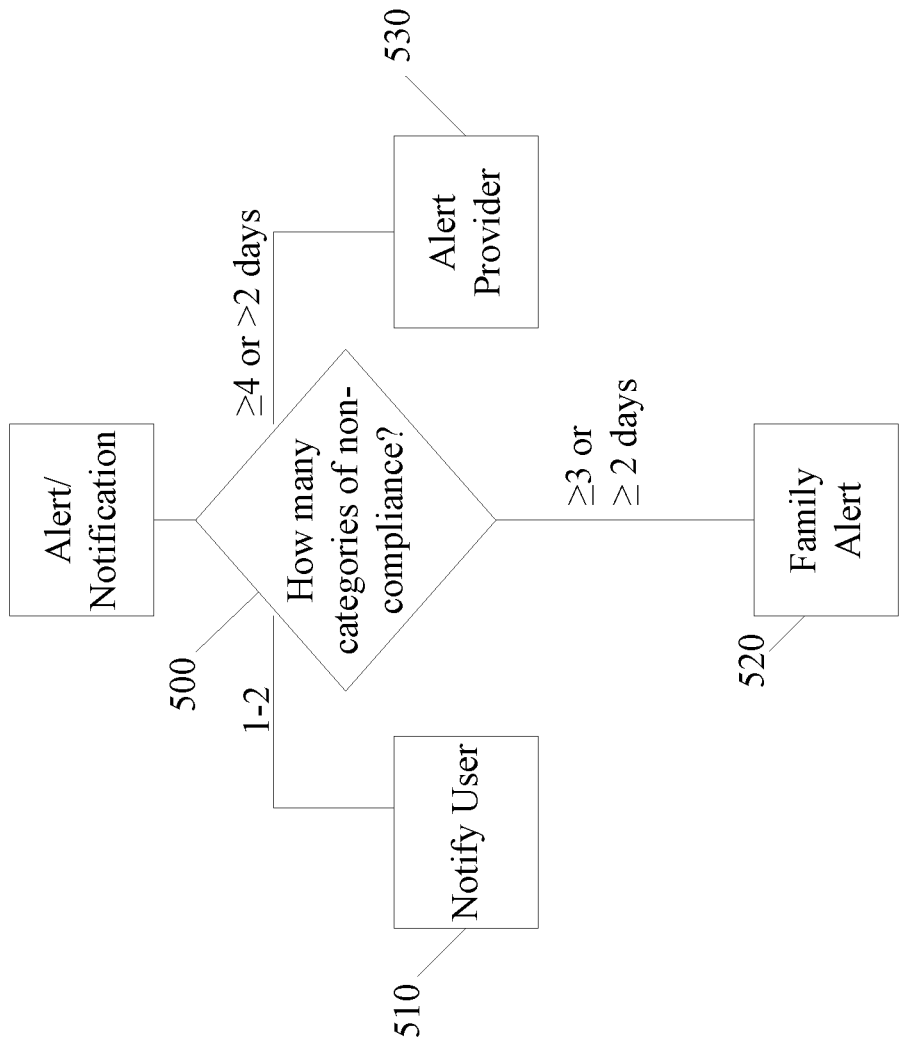
FIG. 5 shows a flowchart of the alert system.

The system will also include an alert system, shown at 260 in FIG. 2, and shown in FIG. 5. The alert/notification system is based on how well the user complies with their assignments and set routine and provides different levels of alert based on their departure from the desired behavior. The amount by which users deviate from the compliance requirements determines who among the different tiers of people will be notified. The alert system will work differently based on the individual, but one embodiment operates as follows.

At 500 in FIG. 5, the system determines how many categories of noncompliance exist for the user, and sets the kind of alert based on how much noncompliance exists.

1) If the user fails to comply with one to two categories of any of the seven categories (sleep, diet, screen time, exercise, social interaction, medication, and academic performance) consistently for two days, only the user is notified at 510.

2) If the user fails to follow their set directions in three or more categories (sleep, diet, screen time, exercise, social interaction, medication, and academic performance) consistently for two days, the user's family or parent/guardian are notified at 520 and asked to more closely monitor the user's behavior and actions.

3) If there are any serious red flags such as sudden changes in behavior for two or more days, a sudden drop in academic performance, or violation of more than four categories consistently, the user's healthcare provider is notified at 530.

Overall, this embodiment serves as a supportive tool for the user. It is not meant to replace other forms of therapy or treatment, however, it is meant to make the user's life easier and put the user more in control. Additionally, the embodiment can motivate the user to achieve independence as opposed to reliance on medications. The app hopes to truly reduce depression in teens and young adults by helping them manage signs and symptoms and allow them to live happy and normal lives.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A system of monitoring and treating depression in a user, comprising:
a computer system, running a computer application,
the computer system including a mobile device associated with the user,
the computer system operating to initially calibrate, to determine baseline information about the user for each of a plurality of different categories of action of the user, and the computer system using the baseline information to determine baseline user behavior, for each of the different categories,
after the initially calibrate, the computer system operating to monitor said each of said different categories of action of the user to obtain monitored information, and to compare the monitored information for monitored categories with the baseline information, and to determine, for each of the monitored categories, whether the user is complying by acting within specified parameters within at least one category, by using a camera on the mobile device to image the user, including at least all of:

1) using the camera to detect weight loss or weight gain, to diagnose that the user's dietary habits need to be adjusted;

2) using the camera to image the user's face to detect discoloration in the user's face to diagnose stress from the discoloration;

3) using the camera to image the user's face to detect when the user has been crying, to diagnose social issues with the user;

4) using the camera to image the user's face to detect a user with baggy eyes and dark lines, to determine that the user's sleep schedule needs to be adjusted; and 5) using the camera to image the user's eyes, to determine dilated eyes to diagnose excitement, and to determine pupils which are contracted to diagnose anger;

the computer system providing positive reinforcement for at least one of the categories in which the user is complying within the category by acting within the specified parameters within the at least one category;

the computer system providing at least one alert for at least another of the categories in which the user is not complying within the category by not acting within specified parameters within the at least another category; and the computer system carrying out an enforcement routine to control at least one controllable device to enforce compliance with a category based on determining that the user is not complying with the category.

2. The system as in claim 1, wherein the enforcement comprises using smart home control to enforce sleeping time and wake up time of the user by controlling at least lightning in the smart home.

3. The system as in claim 1, wherein the enforcement comprises blocking applications from running once a screen time limit has been reached.

4. The System as in claim 1, further comprising diagnosing that the user is feeling good and not depressed, and obtaining facial expressions associated with a time the user is feeling good, and adding the facial expressions to a database of not depressed facial expressions, and later using the facial expressions to diagnose the user being not depressed.

5. The system as in claim 4, wherein the categories of action being done by the user relate to the user's diet, medication compliance, an amount of time the user spends on a computer, an amount of physical activity, frequency and amount of social interaction, and trends in academic performance.

6. The system as in claim 1, wherein the alert is an alert to a first group of people for a first severity of alarm, and is an alert to a second group of people for a second severity of alarm.

7. The system as in claim 6, wherein the alert to the first group of people is for lack of compliance in less than 2 categories, and where the alert to the second group of people is for lack of compliance in more than 2 categories.

8. A method of monitoring and treating depression in a user, comprising:

using a computer system, running a computer application, to initially calibrate, to determine baseline information about the user for each of a plurality of different categories of action of the user, the categories including at least all of sleep of the user, diet of the user, screen time of the user, exercise of the user, amount of social interaction of the user, and medication taken by the user;

using the computer system with the baseline information to determine user behavior, for each of the different categories;

the computer system operating to monitor said each of said different categories of action of the user and to compare monitored categories with the baseline information, and to determine, for each of the categories, whether the user is complying by acting within specified parameters within the category, using information from the initially calibrate;

providing positive reinforcement for at least one of the categories in which the user is complying within the category by acting within the specified parameters within the at least one category by using a camera on the mobile device to image the user, including at least all of:

1) using the camera to detect weight loss or gain, to diagnose that the user's dietary habits need to be adjusted;

2) using the camera to image the user's face to detect discoloration in the user's face to diagnose stress from the discoloration;

3) using the camera to image the user's face to detect when the user has been crying, to diagnose social issues with the user;

4) using the camera to image the user's face to detect a user with baggy eyes and dark lines, to determine that the user's sleep schedule needs to be adjusted; and 5) using the camera to image the user's eyes, to determine dilated eyes to diagnose excitement, and to determine pupils which are contracted to diagnose anger; and providing at least one alert for at least another of the categories in which the user is not complying within the category by not acting within specified parameters within the at least another category; and carrying out an enforcement routine to control at least one controllable device to enforce compliance with a category based in determining that the user is not complying with a category.

9. The method as in claim 8, wherein the enforcement comprises using smart home control to enforce sleeping time and wake up time of the user by controlling at least lightning in the smart home.

10. The method as in claim 8, wherein the enforcement comprises blocking applications from running once a screen time limit has been reached.

11. The method as in claim 8, further comprising diagnosing that the user is feeling good and not depressed, and obtaining facial expressions associated with a time the user is feeling good, and adding the facial expressions to a database of not depressed facial expressions, and later using the facial expressions to diagnose the user being not depressed.

12. The method as in claim 11, wherein the categories of action being done by the user relate to an amount of time the user spends on a computer, exercise, social interaction, and academic performance.

13. The method as in claim 8, wherein the alert is an alert to a first group of people for a first severity of alarm, and is an alert to a second group of people for a second severity of alarm.

14. The method as in claim 13, wherein the alert to the first group of people is for lack of compliance in less than 2 categories, and where the alert to the second group of people is for lack of compliance in more than 2 categories.

* * * * *